United States Patent
Kuester

(10) Patent No.: US 10,912,507 B2
(45) Date of Patent: Feb. 9, 2021

(54) SKIN PRICKING DEVICE

(71) Applicant: OWEN MUMFORD LIMITED, Oxfordshire (GB)

(72) Inventor: Stephen Michael Kuester, Oxfordshire (GB)

(73) Assignee: Owen Mumford Limited, Oxford (GB)

( * ) Notice: Subject to any disclaimer, the term of this patent is extended or adjusted under 35 U.S.C. 154(b) by 282 days.

(21) Appl. No.: 15/537,676

(22) PCT Filed: Oct. 7, 2015

(86) PCT No.: PCT/GB2015/052927
§ 371 (c)(1),
(2) Date: Jun. 19, 2017

(87) PCT Pub. No.: WO2016/102914
PCT Pub. Date: Jun. 30, 2016

(65) Prior Publication Data
US 2017/0347934 A1    Dec. 7, 2017

(30) Foreign Application Priority Data
Dec. 23, 2014   (GB) .................................. 1423125.2

(51) Int. Cl.
*A61B 5/151*   (2006.01)
*A61B 5/15*    (2006.01)

(52) U.S. Cl.
CPC .... *A61B 5/15144* (2013.01); *A61B 5/150022* (2013.01); *A61B 5/15113* (2013.01);
(Continued)

(58) Field of Classification Search
CPC .......... A61B 5/15144; A61B 5/150022; A61B 5/150114; A61B 5/150412;
(Continued)

(56) References Cited

U.S. PATENT DOCUMENTS

2004/0102802 A1*  5/2004  Marshall .......... A61B 5/150022
                                            606/182
2006/0129172 A1*  6/2006  Crossman .......... A61B 5/15142
                                            606/181
(Continued)

FOREIGN PATENT DOCUMENTS

EP    0 403 873 A1    12/1990
EP    2 016 900 A1    1/2009
(Continued)

OTHER PUBLICATIONS

International Search Report, dated Feb. 12, 2016, from corresponding PCT/GB2015/052927 application.
(Continued)

*Primary Examiner* — Matthew Kremer
*Assistant Examiner* — Avery M Foley
(74) *Attorney, Agent, or Firm* — Quarles & Brady LLP

(57) ABSTRACT

A skin pricking device includes a housing having an opening formed in a proximal end thereof; a spring mounted lancet including a needle within a casing having body and cap parts, interconnected by a separable coupling. The cap part has a cap projecting through the opening allow a user to grip and remove the cap. The device further includes a trigger for firing the lancet. Turning the cap part moves the entire lancet, engaging a trigger stop surface on the distal body part of the lancet with a trigger catch and further biasing the trigger to block the lancet. Further turning of the cap part over a second angle relative to the housing causes the cap part to move in a proximal direction by a further, second distance, thereby axially separating the cap part from the body part, whereby the cap part can then be removed from the device.

13 Claims, 7 Drawing Sheets

(52) U.S. Cl.
CPC .... *A61B 5/150114* (2013.01); *A61B 5/15117* (2013.01); *A61B 5/150412* (2013.01); *A61B 5/150549* (2013.01); *A61B 5/150916* (2013.01)

(58) Field of Classification Search
CPC ........ A61B 5/150549; A61B 5/150916; A61B 5/15113; A61B 5/15117; A61B 5/150183; A61B 5/5019; A61B 5/150297; A61B 5/150541; A61B 5/151
See application file for complete search history.

(56) References Cited

U.S. PATENT DOCUMENTS

| | | | |
|---|---|---|---|
| 2009/0275860 A1* | 11/2009 | Nakamura | A61B 5/15142 600/573 |
| 2011/0264131 A1* | 10/2011 | Sun | A61B 5/1411 606/182 |
| 2012/0203259 A1 | 8/2012 | Saeki et al. | |
| 2012/0215246 A1* | 8/2012 | Hyoue | A61B 5/1411 606/182 |
| 2013/0158586 A1* | 6/2013 | Pusey | A61B 5/15117 606/173 |
| 2014/0052024 A1* | 2/2014 | Nicholls | A61B 5/150549 600/583 |

FOREIGN PATENT DOCUMENTS

| | | |
|---|---|---|
| EP | 2 486 852 A1 | 8/2012 |
| GB | 2 487 188 A | 7/2012 |
| WO | 2004/080305 A1 | 9/2004 |
| WO | 2012/09326 A1 | 7/2012 |

OTHER PUBLICATIONS

GB Search Report, dated Jun. 23, 2015, from corresponding GB1423125.2 application.

* cited by examiner

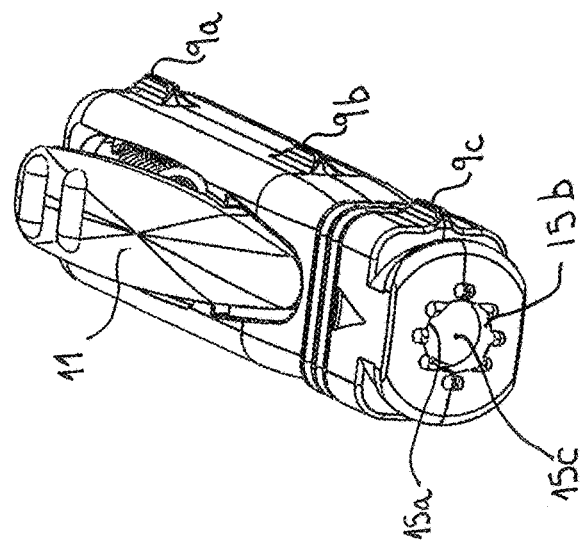
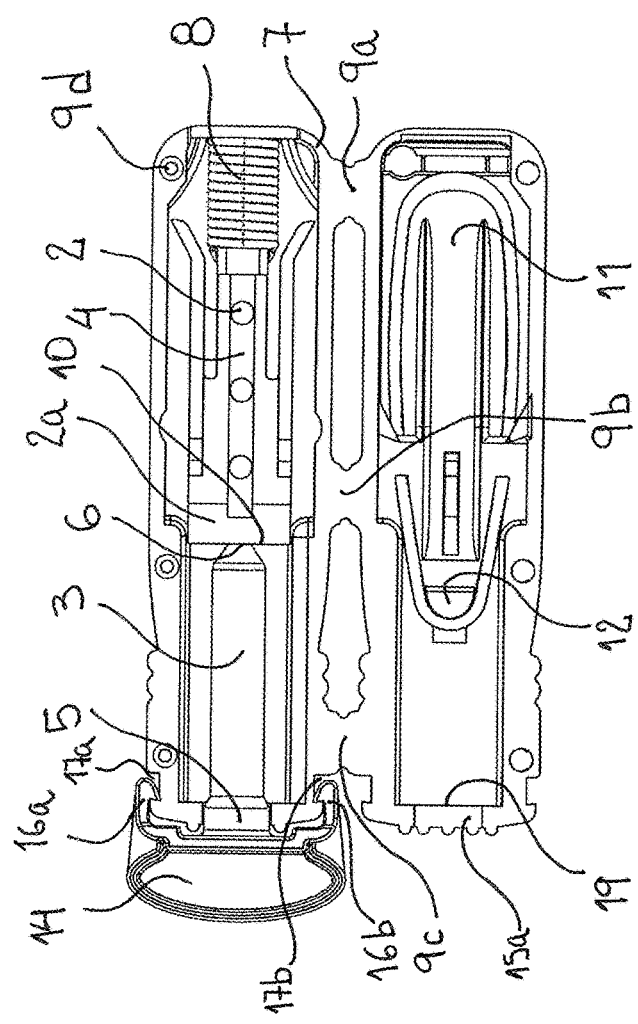
FIG. 2
FIG. 1

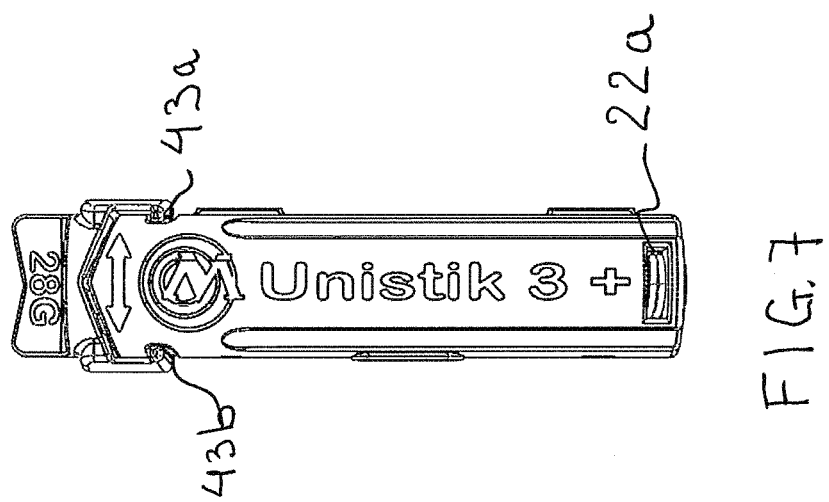

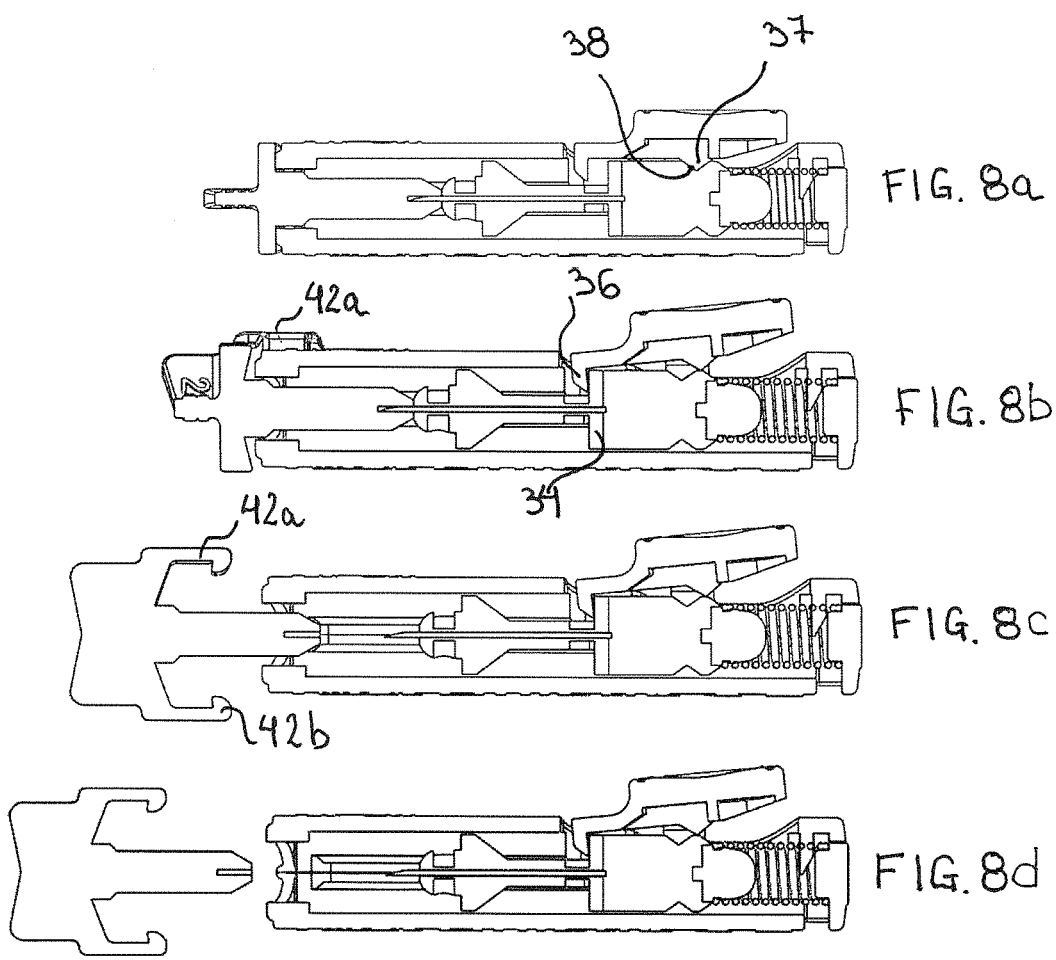

SKIN PRICKING DEVICE

TECHNICAL FIELD

The present invention relates to a skin pricking device and more specifically to a single-use skin pricking device having a cap that is twisted off in order to prepare the device for firing.

BACKGROUND

It is often required to take small samples of blood from a subject for the purpose of testing or analysing the blood. A common way of achieving this is by using a small needle to pierce the skin at a location where blood vessels are close to the surface. The combination of a needle and its holder is commonly known as a "lancet". In order to avoid infection and contamination, lancets are preferably intended for single use and are disposable. They must therefore be compact, to allow users to carry multiple lancets on their person, and cheap to manufacture.

There are a large number of disposable lancets currently on the market, which include the Unistik™ manufactured and marketed by Owen Mumford Ltd (Woodstock, UK). The Unistik device 1 is illustrated in FIGS. 1 and 2 and comprises a lancet 2a having a needle 2 moulded within a plastic casing 3. Hereinafter, the terms "proximal" and "distal" are used to describe parts of the device that are respectively close to or distant from the skin when the device is operating. The casing 3 has a distal body part 4 and a proximal cap part 5, with the body and cap parts being connected via a separable, e.g. frangible, coupling 6. The lancet is loaded into a two sided housing 7, with a spring 8 being located between the distal end of the lancet and a rear inner surface of the housing. The spring is compressed during the loading operation. The two housing sides are folded around the lancet and spring, about hinges 9a, 9b and 9c with the two sides of the housing fitting together via closure pegs 9d to leave the lancet in a primed, ready to fire state. The closure pegs are located on the side of the housing opposite to the hinges. The casing is provided with a stop surface 10. A trigger 11 is formed in the housing 7 and provides an inwardly biased catch 12. This catch engages with the stop surface 10 provided on the casing 3 when the lancet is in the primed state.

Considering further the cap part 5 of the casing, this has a cap 14 that remains outside of the housing after the housing sides are folded over and fitted together. Cut-outs 15a, 15b at the proximal ends of the housing sides combine to create an aperture 15c. The cap has a flattened end surface for gripping by a user. It will be further appreciated from FIG. 1 that, when the housing sides are folded over about the lancet, a pair of legs 16a, 16b projecting from the cap in the distal direction, are caught within respective recesses 17a, 17b formed in a proximal outer surface of the housing 7. These recesses each have an angular extent of approximately 90 degrees.

In order to prepare the lancet for use, a user holds the housing in the fingers of one hand and grips the cap with the fingers of the other, and twists the cap relative to the housing until the legs of the cap are released from their recesses. This action should break the separable coupling between the two casing parts. The user then pulls the cap to withdraw the entire cap part from the housing, presses the proximal end of the housing against his or her skin, and depresses the trigger. This moves the catch outwardly, releasing the stop surface and allowing the spring to expand and push the needle and remaining casing part in the proximal direction. The needle and body part proceed until the stop surface 10 hits the inwardly facing surface 19 at the proximal end of the housing. The dimensions of the needle and body part of the casing are such that, at this point, the tip of the needle projects out of the opening 15c by a small amount, e.g. 1.8-2 mm, pricking the user's skin and drawing a small amount of blood. The device is also dimensioned such that at this point the spring is slightly over extended. The spring therefore contracts back on itself, withdrawing the tip of the needle back into the housing. This action avoids a "dirty" needle from subsequently presenting a stick injury and/or contamination hazard.

A potential problem with the prior art devices is that the user action of twisting the cap may not completely break the separable coupling. This may happen for example if the user twists the cap only a small amount, e.g. one quarter turn. If the user then pulls the cap from the housing, this may cause the entire lancet to be pulled out to some extent: the trigger catch may not be strong to hold the casing and it will just be "flicked" outwardly. If this happens, the device is effectively useless and must be discarded.

SUMMARY

According to a first aspect of the invention, there is provided a skin pricking device comprising a housing having an opening formed in a proximal end thereof; a lancet, spring mounted within the housing, the lancet comprising a needle contained within a casing having a distal body part and a proximal cap part, the body part and the cap part being connected by a separable coupling, and the cap part having a cap that projects through said opening to allow gripping of the cap by a user and removal of the cap part from the lancet by twisting the cap. The skin pricking device further comprising a user actuable trigger for firing the lancet following removal of the cap part, the cap part being configured so that turning of the cap part over a first angle relative to the housing causes the entire lancet to move in a proximal direction by a first distance, thereby bringing a trigger stop surface on the distal body part of the lancet into engagement with a trigger catch of the trigger and further biasing the trigger to block the lancet, and so that further turning of the cap part over a second angle relative to the housing causes the cap part to move in a proximal direction by a further, second distance, thereby axially separating the cap part from the body part, whereby the cap part can then be removed from the device.

Certain embodiments of the invention provide the lancet as a needle contained within a plastics casing having a distal body part and a proximal cap part, wherein the cap part can be removed from the lancet by twisting and pulling off the cap until the cap is completely removed from the device.

Embodiments provide the cap part with one of co-operating cam surfaces and cam followers and a proximal surface of the housing with the other of co-operating cam surfaces and cam followers, such that turning of the cap part over first and second angles causes the cap part to move in a proximal direction with respect to the housing. Moreover, the co-operating cam surfaces and cam followers are provided by opposed surfaces on an outer and proximally facing surface of the housing, surrounding the opening, and on a distally facing surface of the cap.

In a preferred embodiment, said cap comprises a flattened end part and a pair of flexible fingers, which depend from the flattened end part in a distal direction. The proximal end of the housing has formed a pair of receptacles, which receive the tips of the flexible fingers in order to retain the cap part prior to its rotation over said first and second angles.

In a preferred embodiment of the invention, a fire stop surface on said distal body part of the lancet is axially spaced from the trigger stop surface in the proximal direction, and it is configured to cooperate with a feature that is provided on the housing to stop the lancet after firing. Said feature comprises a nib that tapers in the distal direction.

In a preferred embodiment of the invention, there is provided a boss, formed on an inner surface of the housing at its distal end, and a spring located at a first end over the boss and having its second end in contact with a distal end of the lancet.

In a preferred embodiment of the invention, said trigger is coupled to the housing by a pair of legs that provide pivot points about which the trigger can pivot relative to the housing, with a trigger catch being provided on an inwardly facing surface of the trigger on the proximal side of said legs. Preferably, the legs are flexible to allow the trigger to pivot relative to the housing. More preferably, the trigger comprises one or more teeth projecting inwardly into the housing from said inwardly facing surface of the trigger on the distal side of the legs. Moreover, the body part of the casing is provided with one or more recesses for cooperating with the or each teeth, whereby said biasing of the trigger to block the lancet is brought about by the or each tooth being pushed out of the cooperating recess as the entire lancet is moved in a proximal direction by said first distance.

In a preferred embodiment of the invention, said housing comprising first and second housing parts coupled by one or more hinges to allow the housing to be folded around the lancet.

In a preferred embodiment of the invention, said separable coupling is provided by a narrowing of the casing at the junction between the body part and the cap part.

According to a second aspect of the invention, there is provided a skin pricking device comprising a housing having an opening formed in a proximal end thereof; a lancet, spring mounted within the housing, the lancet comprising a needle that is contained within a casing that has a distal body part and a proximal cap part. The body part and the cap part is connected by a separable coupling, and the cap part having a cap that projects through said opening to allow gripping of the cap by a user and removal of the cap part from the lancet by twisting the cap. The skin pricking device further comprising a user actuable trigger, for firing the lancet following removal of the cap part, and a fire stop surface on said distal body part of the lancet, the fire stop surface being axially spaced from the trigger stop surface in the proximal direction and being configured cooperate with a nib, which is provided on the housing to stop the lancet after firing, and which is tapering in the distal direction.

Certain embodiments provide the lancet as a needle contained within a plastics casing having a distal body part and a proximal cap part, wherein the cap part can be removed from the lancet by twisting and pulling off the cap until the cap is completely removed from the device.

According to a third aspect of the present invention, there is provided a skin pricking device comprising a housing having an opening formed in a proximal end thereof; a lancet, spring mounted within the housing, the lancet comprising a needle that is contained within a casing having a distal body part and a proximal cap part. The body part and the cap part being connected by a separable coupling, and the cap part having a cap that projects through said opening to allow gripping of the cap by a user and removal of the cap part from the lancet by twisting only or by twisting and pulling off the cap. The skin pricking device further comprises a user actuable trigger for firing the lancet, following removal of the cap part, which provides a trigger catch for engaging with a trigger stop surface on the distal body part of the lancet. The skin pricking device also further comprises a fire stop surface on said distal body part of the lancet, the fire stop surface being axially spaced from the trigger.

Certain embodiments provide the lancet as a needle contained within a plastics casing having a distal body part and a proximal cap part, wherein the cap part can be removed from the lancet by twisting and pulling off the cap until the cap is completely removed from the device.

BRIEF DESCRIPTION OF THE DRAWINGS

FIGS. 1 and 2 illustrate a prior art skin pricking device;

FIG. 7 is a still further perspective view of the skin pricking device of FIG. 3 with the housing closed; and FIGS. 8a to 8d illustrate distinct operational states of the skin pricking device of FIG. 3.

DETAILED DESCRIPTION

Figure 3:
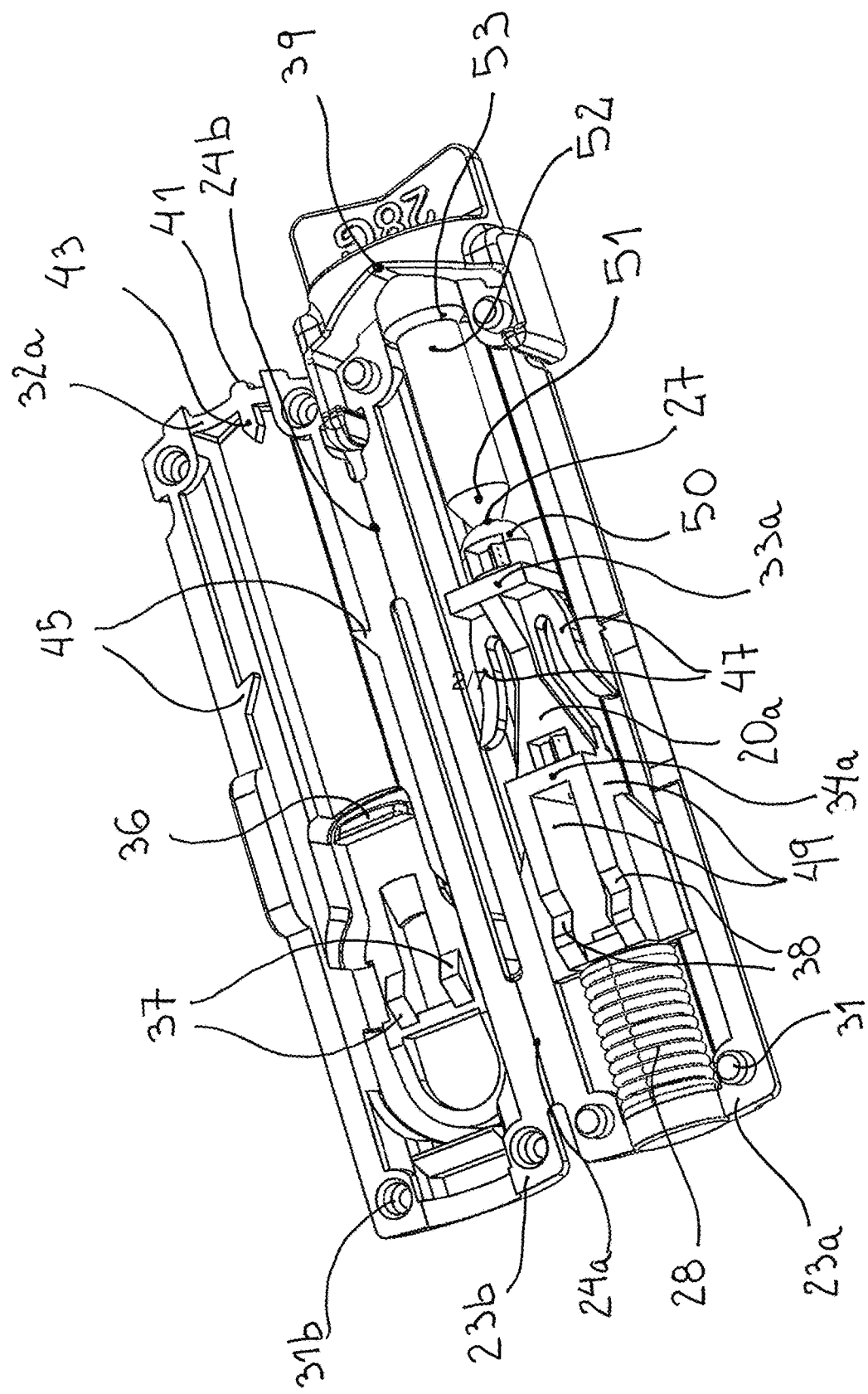
FIG. 3 is a perspective view of a single use skin pricking device with a housing in an unclosed state.
Figure 4:
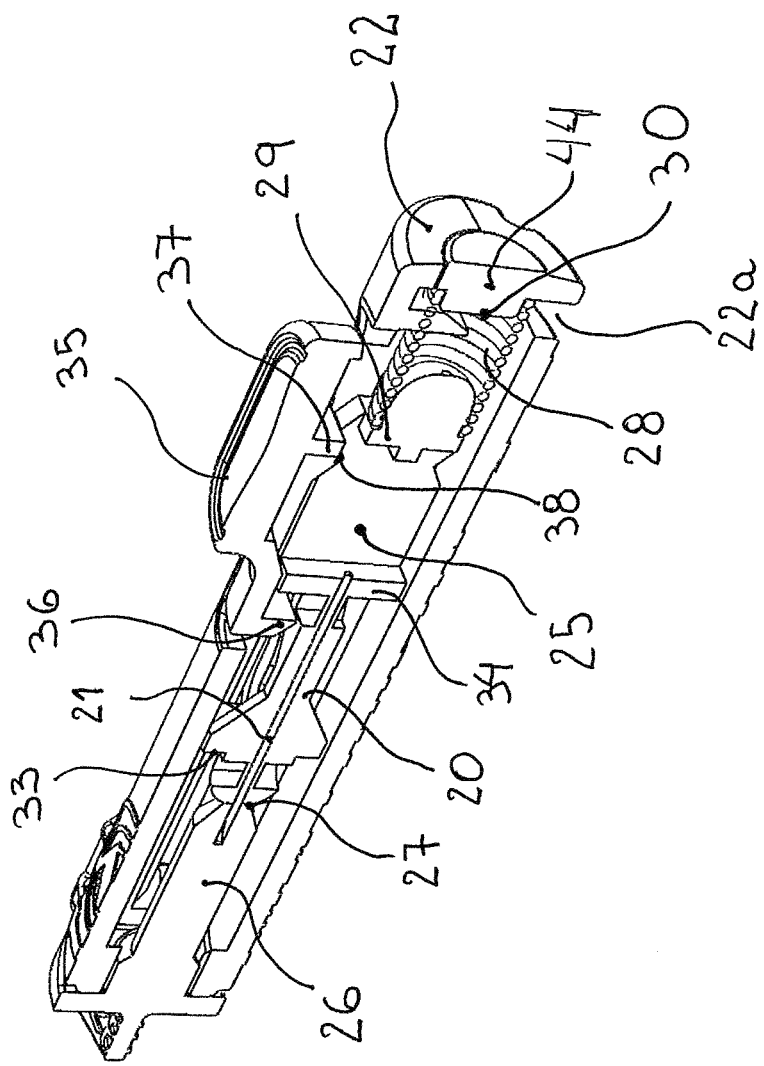
FIG. 4 is a partial cross-sectional view of the skin pricking device of FIG. 3.
Figure 5:
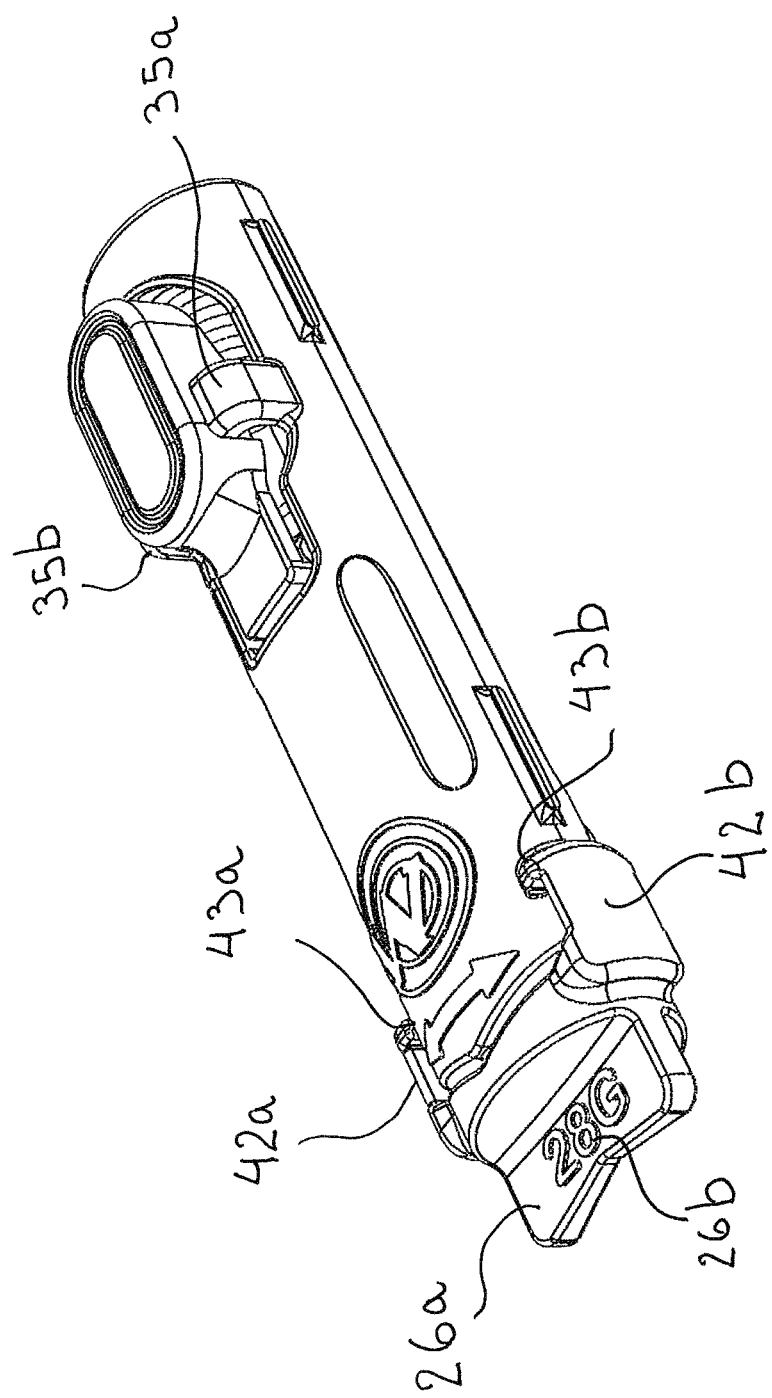
FIG. 5 is a perspective external view of the skin pricking device of FIG. 3 with the housing closed.
Figure 6:
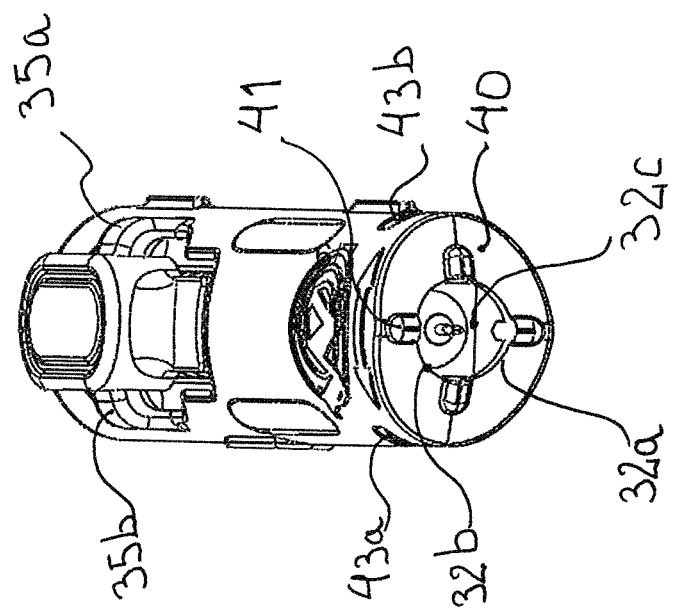
FIG. 6 is a further perspective view of the skin pricking device of FIG. 3 with the housing closed.

A known skin pricking device has been described above with reference to FIG. 1. An improved skin pricking device is illustrated in FIGS. 3 to 7. For the purpose of this description, the proximal end of the device is that end that is closest to the skin in use, i.e. the left hand side as viewed in FIG. 1, whilst the distal end of the device is that end that is furthest from the skin in use, i.e. the left hand side as viewed in FIG. 3. A housing 22 of the device comprises two sides, an underside 23a and a topside 23b, which can be folded about a pair of hinges 24a and 24b to encase a lancet 20a and spring 28. The spring's 28 distal end is located on a boss 44, which extends inwardly from the distal end of the underside 23a. A slot 22a is present in the underside directly beneath the boss. This slot allows for a component of the mold to enter into the housing during the molding process in order to form the opposed surface of the boss.

The underside 23a is also provided with upwardly projecting pegs 31 on all four corners, whilst complementary receptacles are provided at the four corners of the topside 23b. When the housing is closed about the lancet and spring, the pegs press into the respective receptacles in order to secure the housing in place. The presence of pegs on both sides of the housing maintains the housing in place even if the hinges break. Furthermore, topside 23b comprises two opposed, inwardly projecting triangular-shaped teeth 45, each tooth providing a retraction stop surface facing in the proximal direction, which prevents the device from being reused.

The proximal end of each housing side is provided with cut-outs 32a, 32b such that, when the casing sides are folded together, the cut-outs 32a, 32b combine to create a generally circular aperture 32c through which the needle tip can pass when the device is fired. A nib 43, which tapers inwardly in the distal direction, is provided at the back surface of the proximal end's topside and underside. The proximally facing outer surface of the housing sides present a substantially V-shaped (slightly curved on its sides) surface. When the sides are folded over to close the housing, the outer surface of the housing thus presents a pair of cam surfaces that co-operate with a cap as will be described below.

A trigger 35 is formed integrally with the topside of the housing, such that the trigger is connected to the topside 23b by a pair of opposed legs 35a, 35b. The legs are integrally moulded with the topside 23b. An inwardly facing catch 36 and an inwardly projecting pair of transversely spaced teeth 37 are provided on the inwardly facing surface of the trigger, with the catch being spaced axially from the teeth, along the length of the trigger.

Considering now the lancet 20a, this comprises a needle 21 encased within a molded unitary casing 20 made of plastics. The casing has two parts: a distal body part 25 and a proximal cap part 26, which are connected via a separable, e.g. frangible, coupling 27. This coupling provides a shear point, where the cap part is axially separated from the distal body part by twisting the cap part. The axial separation is controlled to provide a clean break without shards. The casing is moulded over the needle 21 in a clean room environment and the casing is later sterilised by irradiation using a separate process. This renders the needle 21 sterile inside the casing 20.

The distal body part has a generally rectangular cross-section, with a boss projecting axially from its distal end. Close to its distal end, a pair of triangular indents 38 is provided in two parallel and axially extending sidewalls 49 of the part. The sidewalls terminate at a first wall 34a that is perpendicular both to the sidewalls and to the direction of insertion of the lancet. The first wall provides, on its proximal side, a stop surface 34. An elongate intermediate portion of the distal part extends between the first wall 34a and a second wall 33a. The second wall provides a proximally facing surface 33 that operates as a fire stop surface as will be described further below. A dome shaped head 50 extends from the second wall to the location of the separable coupling 27. A pair of flexible legs 47 depends from the second wall 33 in the distal direction, both legs flaring outwardly from the lancet axis.

Considering now the proximal cap part 26 from its distal end to its proximal end, a cone shaped section 51 extends from the separable coupling, with its narrowest point being at the coupling and being connected to the dome shaped head of the body part. The enlarged end of cone shaped section 51 is further connected to cylindrical region 52, which extends from the enlarged end of the cone, to a further frustoconical region 53 which enlarges the cylindrical part. The enlarged cylindrical part then extends into a cap 26a. The cap has a flattened end surface for gripping by a user. A needle gauge size 26b may be printed or embossed on this flattened part to provide visual information to the user. Two diametrically opposed flexible fingers 42a and 42b project in a distal direction from the lancet cap 26a over the outside of the housing.

Considering further the cap 26a, the distally facing surface has a saddle-like shape, narrowing from the outermost edges to the centre. This provides a pair of cam followers which co-operate with cam surfaces of the housing as will be described further below.

When the skin pricker is assembled, the lancet 20a is loaded into the housing 22, together with a spring 28, which is located and compressed between the distal end of the body part 29 and a distal inner surface 30 of the housing 22.

FIGS. 8a to 8d will now be used to illustrate the operation of the improved skin pricking device. FIG. 8a shows the skin pricker in its assembled and unfired state, with teeth 37 and triangular indents 38 interlocked. In this state there is no external stress on the legs 35a, 35b. However, in alternative embodiments of the invention, the legs may be stressed when the device is in its assembled state.

Considering now the operation of the skin pricking device, a user holds the skin pricking device in one hand, grips the cap with the other and twists the cap relative to the housing over approximately 45 degrees or one eighth turn, achieving the state illustrated in FIG. 8b. This unlocks the two flexible fingers 42a, 42b from receptacles 43a, 43b. As a result of this action, the cam followers of the cap are pushed outwardly by the cam surfaces on the outer surface of the housing, allowing the spring to expand axially and moving the entire lancet in a proximal direction by a first distance. As this happens, the teeth 37 on the underside of the trigger slide out of the triangular indents 38 and the trigger stop surface 34 on the distal body part of the lancet is brought into engagement with the trigger catch 36. As the teeth 37 are moved outwardly in a transverse direction during this operation, this applies a rotational force to the trigger that acts about a pivot axis formed by the legs 35a, 35b, biasing the catch 36 inwardly to reinforce the blocking force applied by the catch to the trigger stop surface 34 of the lancet.

As the user continues to turn the cap over a second angle relative to the housing, e.g. a further one eighth turn or more (at this stage, as the fingers of the cap have moved axially with respect to the housing, the ends of the fingers 42a, 42b can no longer re-engage with the receptacles 43a, 43b), the cap part moves in a proximal direction by a further second distance. As the lancet is blocked by the trigger (engagement of the catch with the trigger stop surface), this results in axially separating the cap part from the distal body part. This state is illustrated in FIG. 8c.

The user can now completely remove the cap part from the housing 22. This state is illustrated in FIG. 8d. At this point, the end tips of the flexible legs 47 formed on the lancet have not yet passed beyond the teeth 45 formed on the inner surface of the housing.

The user then presses the proximal end of the device against his or her skin. The presence of a series of bumps 41 on the proximal end of the housing may de-sensitise the user's skin to some extent. He or she then presses inwardly on the rear end of the trigger 35, which results in the inwardly biased catch 36 being released and the lancet being fired. On firing, the lancet is driven forward by the extending spring 28 through the housing 22 in the proximal direction. As it does so, the legs 47 flex inwardly as their end tips pass over the teeth 45, snapping back in front of the teeth. As the lancet continues to move in the proximal direction, the tip of the needle 21 passes through the opening 32c in the housing and penetrates the user's skin. Movement of the lancet continues until the fire stop surface 33 of the lancet casing is brought into contact with the nib 43. The fine tip of the nib will "crumple" very slightly as a result of this impact, bringing the lancet to a stop over a very small distance. However, this is sufficient to damp the impact, resulting in a reduction in the noise that would otherwise result from the impact.

At this stage, the spring 28 is overextended to some degree and, as a result, contracts slightly to pull the needle tip back through the aperture 32c into the housing. The needle tip is thereby secured within the housing 22 after use, preventing any inadvertent needle stick injuries. However, retraction of the lancet into the housing is limited by the outwardly sprung legs 47 abutting the teeth 45. This effectively prevents re-use of the device.

It will be appreciated from the discussion above that, as the distal body part of the lancet is blocked by the trigger catch after the first part turn of the cap, and in this state the trigger is biased inwardly to enhance the blocking effect, the user cannot at this stage pull the entire lancet out of the housing. It requires the user to further twist the cap, thus completely separating the casing parts, before the cap part can be pulled out of the housing to expose the tip of the needle. Moreover, because the trigger stop and the fire stop are axially spaced, the mechanism allows for a small-sized trigger, which can be placed at the rear of the pricking device. This gives more space at the proximal end of the housing for a user to grip the housing whilst removing the cap part, helping to avoid any accidental operation of the trigger during cap removal.

It will be appreciated by those skilled in the art that various modifications may be made to the above described embodiment without departing from the scope of the present invention.

The invention claimed is:

1. A skin pricking device, comprising:
  a housing (22) having an opening (32c) formed in a proximal end thereof;
  a lancet (20a) that is mounted within the housing with a spring (28) bearing thereon, the lancet comprised of a needle (21) contained within a casing (20) having a distal body part (25) and a proximal cap part (26), the body part and the cap part being connected by a separable coupling (27), and the cap part having a cap (26a) that projects through said opening to allow gripping of the cap by a user and removal of the cap part from the lancet by twisting the cap; and
  a user actuable trigger (35) configured for firing the lancet,
  the cap part being configured so that turning of the cap part over a first angle relative to the housing causes an entirety of the lancet to move in a proximal direction by a first distance, thereby pivoting the trigger about an axis from a first position to a second position to bring a trigger stop surface (34) on the distal body part of the lancet into engagement with a trigger catch (36) of the trigger and to bias the trigger to block the lancet from being fired, and being configured so that further turning of the cap part over a second angle relative to the housing causes the cap part to move in the proximal direction by a further second distance, thereby axially separating the cap part from the body part, whereby the cap part is then removable from the device.

2. The device according to claim 1, the cap part being provided with one of co-operating cam surfaces and cam followers, and a proximal surface of the housing being provided with the other of the co-operating cam surfaces and the cam followers, such that said turning of the cap part over said first and second angles causes the cap part to move in the proximal direction.

3. The device according to claim 2, wherein the other of said co-operating cam surfaces and cam followers are provided on an outer and proximally facing surface of the housing, surrounding said opening, and the one of said co-operating cam surfaces and cam followers are provided on a distally facing surface of said cap (26a), the outer and proximally facing surface of the housing and the distally facing surface of said cap being opposed surfaces.

4. The device according to claim 1, wherein said cap (26a) comprises a flattened end part and a pair of flexible fingers (42a, 42b) depending from the flattened end part in a distal direction, the proximal end of the housing having formed thereon a pair of receptacles (43a, 43b) receiving tips of the flexible fingers (42a, 42b) in order to retain the cap part prior to a rotation of the cap part over said first and second angles.

5. The device according to claim 1, further comprising:
  a fire stop surface (33) on said distal body part (25) of the lancet, the fire stop surface (33) being axially spaced from the trigger stop surface (34) in the proximal direction and being configured to cooperate with a structural feature provided on the housing to stop the lancet after firing.

6. The device according to claim 5, wherein said structural feature comprises a nib (43) tapering in a distal direction.

7. The device according to claim 1, further comprising:
  a boss formed on an inner surface of the housing at a distal end thereof,
  a first end of the spring provided over the boss and a second end of the spring in contact with a distal end of the lancet.

8. The device according to claim 1, wherein said trigger (35) is coupled to the housing by a pair of legs (35a, 35b) providing pivot points about which the trigger can pivot relative to the housing, said trigger catch (36) being provided on an inwardly facing surface of the trigger on a proximal side of said legs.

9. The device according to claim 8, wherein said legs are flexible so as to allow the trigger (35) to pivot relative to the housing.

10. The device according to claim 9, further comprising:
  one or more teeth (37) projecting inwardly into the housing from said inwardly facing surface of the trigger on a distal side of said legs, the body part of the casing being provided with one or more recesses for cooperating with each of the one or more teeth, whereby said biasing of the trigger to block the lancet is brought about by the one or more teeth being pushed out of the cooperating recess as the entirety of the lancet is moved in the proximal direction by said first distance.

11. The device according to claim 1, said housing comprising first and second housing parts coupled by one or more hinges to allow the housing to be folded around the lancet.

12. The device according to claim 1, wherein said separable coupling (27) is provided by a narrowing of the casing at a junction between the body part (25) and the cap part (26).

13. The device according to claim 1, wherein pivoting the trigger from the first position to the second position causes a portion of the trigger to move away from the housing.

* * * * *